US00PP31279P3

(12) United States Plant Patent
Nakagoshi et al.

(10) Patent No.: US PP31,279 P3
(45) Date of Patent: Dec. 24, 2019

(54) BUNASHIMEJI MUSHROOM NAMED 'MARMO22GO'

(50) Latin Name: ***Hypsizygus marmoreus* (Peck) Bigelow**
Varietal Denomination: Marmo22go

(71) Applicant: HOKUTO CORPORATION, Nagano (JP)

(72) Inventors: Ayumi Nakagoshi, Nagano (JP); Megumi Takano, Nagano (JP); Kenji Ouchi, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 0 days.

(21) Appl. No.: 15/932,642

(22) Filed: Mar. 30, 2018

(65) Prior Publication Data

US 2019/0289765 P1 Sep. 19, 2019

(30) Foreign Application Priority Data

Mar. 19, 2018 (JP) ..... PBR 32950

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00; C12N 1/14; C12R 1/645
See application file for complete search history.

*Primary Examiner* — June Hwu
(74) *Attorney, Agent, or Firm* — Konomi Takeshita

(57) ABSTRACT

The present variety of mushroom named 'Marmo22go' was cultivated by the gathering and repeated breeding of Bunashimeji mushrooms having dominant traits, which has good qualitative character and appearance, a thick white stem, a large mushroom size, and a resistance to high temperatures. This edible mushroom is exquisite in stability, reproducibility and uniformity when being produced.

18 Drawing Sheets

BACKGROUND OF THE INVENTION

This invention relates to a new and distinct variety of mushroom of Bunashimeji mushroom, *Hypsizygus marmoreus* (Peck) Bigelow. This new variety named 'Marmo22go' cultivated by repeated breeding of Bunashimeji mushrooms having dominant traits, which has a thick white stem, a large mushroom size, a resistance to high temperatures and ensures presentable stability, reproducibility and uniformity.

Bunashimeji (*Hypsizygus marmoreus*) now boasts of being the second most consumed edible mushroom after enokitake mushroom in Japan. After bunashimeji was cultivated and became available in the market in large quantities, 'Hokuto 8gokin' was developed which reduced the characteristic bitterness of the original bunashimeji. Investigation on tasty bunashimeji was continued even after the development of Hokuto 8gokin, and a variety with improved taste, quality and keeping quality named 'Hokuto 18gokin' was developed, which contributed to an increase in consumption.

In order to further improve cultivation stability and the quality of mushrooms, selective breeding was repeatedly carried out by cross-breeding. As a result, a 'Marmo22go' mushroom was developed with a thick white stem and larger mushroom size, and a greater resistance to high temperatures, as compared to the 'Hokuto 18gokin' mushroom. Subsequently, the stability, reproducibility and uniformity of the variety were verified, and cultivation was completed.

SUMMARY OF THE INVENTION

The present invention is a new and distinct variety of mushroom characterized particularly by its good qualitative character and appearance, a thick white stem, large mushroom size, and a resistance to high temperatures, which can be cultivated by gathering and repeated breeding of fungal strains having dominant traits and is exquisite in stability, reproducibility and uniformity when being produced. This novel and distinct variety of mushroom is identified as 'Marmo22go'.

DETAILED DESCRIPTION OF THE INVENTION

The history of the 'Marmo22go' mushroom in terms of improvement period and the like are set forth in the following chronological list of each stage of variety improvement:

May 2005: Cultivation of 'MH025616' strain.

December 2014: Cultivation of 'MH025615' strain.

January 2017: 'MH025616' and 'MH025615' strains were crossed, and of the obtained strains, a strain of high quality, of the targeted white stem was selected and designated 'MH025617'. Growing test was repeatedly conducted on 'MH025617' and since distinguishability, stability and uniformity were confirmed, the strain was named 'Marmo22go' and cultivation was completed. Dual culture performed for 'Marmo22go' and 'MH025615' and dual culture performed for 'Marmo22go' and 'MH025616' showed formation of a zone line (FIGS. 17A, 17B, 18A, and 18B).

March 2018: Applied for registration of a new variety to the Ministry of Agriculture, Forestry and Fisheries of Japan.

Figure 1:
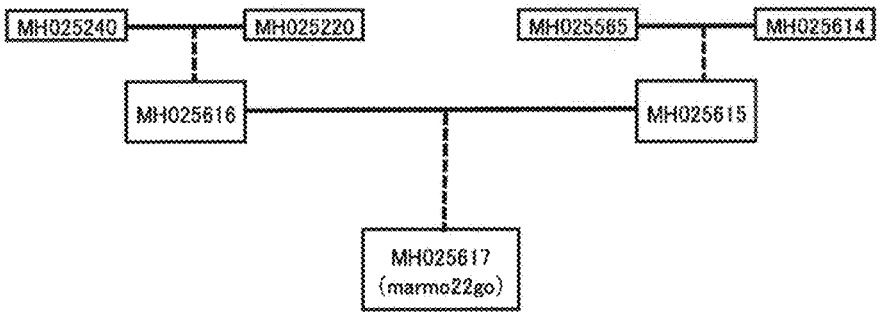
FIG. 1 shows a phylogenetic tree illustrating the antecedents of 'Marmo22go'.

The above crossing is summarized in the phylogenetic tree illustrated in FIG. 1.

The 'Marmo22go' mushroom has the following characteristics: a thick white stem, a large mushroom size, and a resistance to high temperatures.

(1) Comparison with existing variety by dual culture

Dual culture was performed for the 'Marmo22go' mushroom and similar varieties so as to examine whether or not a zone line is formed.

Study method: As an examination method, a potato dextrose agar medium was used, and the 'Marmo22go' mushroom and similar varieties were inoculated thereon face to face at an interval of 3 cm, and then culture was performed at 25° C. for 28 days to examine whether or not a zone line was formed.

Strain used:

'*Marmo*22*go*'.—Present variety.

'*Marmo*23*go*'.—Variety similar to the present variety.

'*Hokuto*18*gokin*'.—Variety similar to the present variety.

Figure 2A:
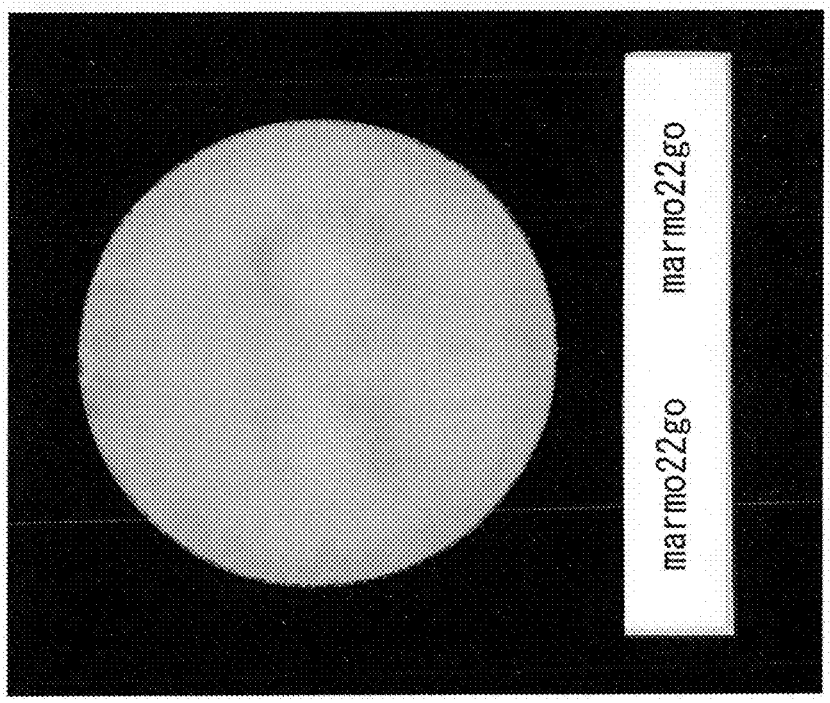
FIGS. 2A and 2B respectively show front and back images of a dual-culture of 'Marmo22go' colony.
Figure 2B:
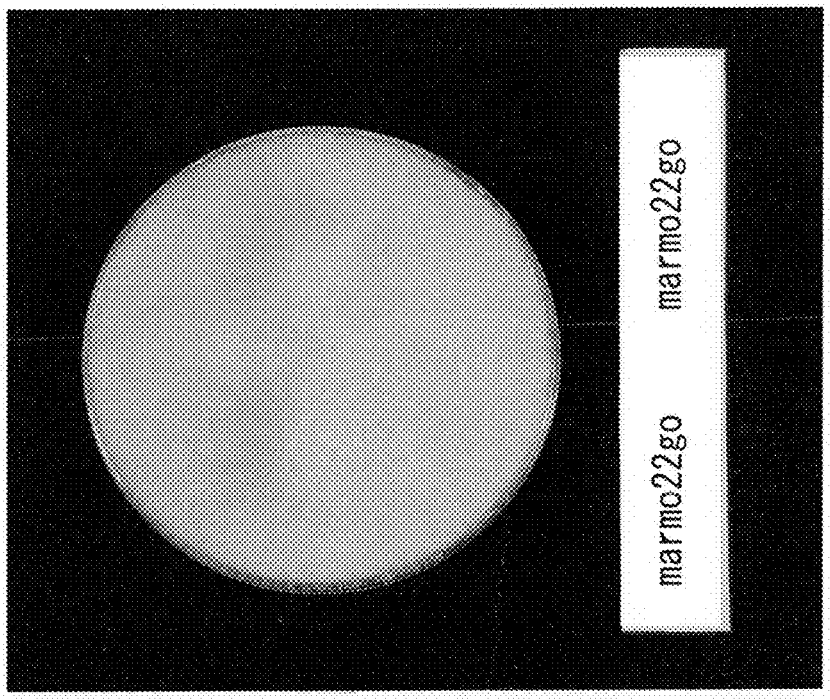
Figure 3A:
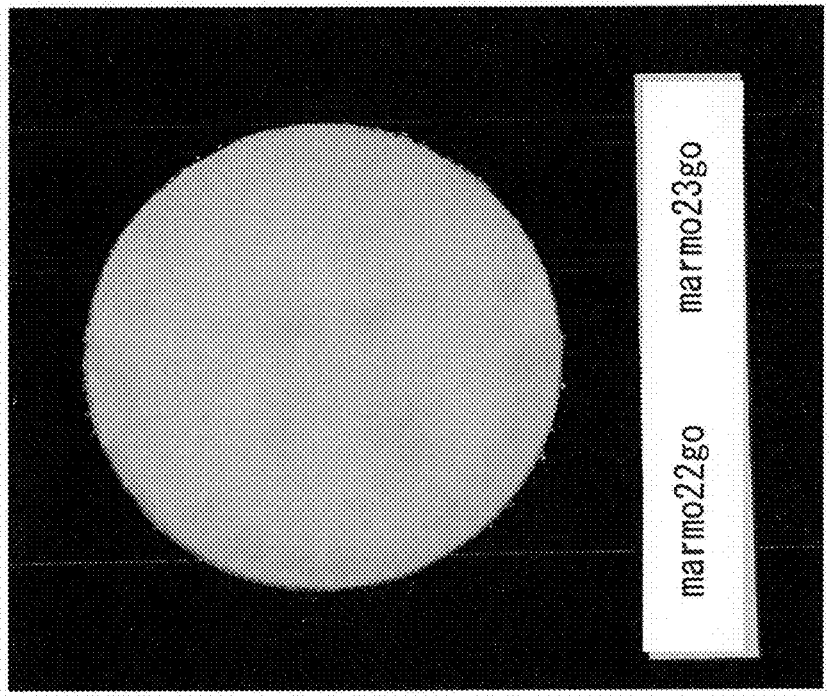
FIGS. 3A and 3B respectively show front and back images of a dual-culture of 'Marmo22go' and 'Marmo23go'.
Figure 3B:
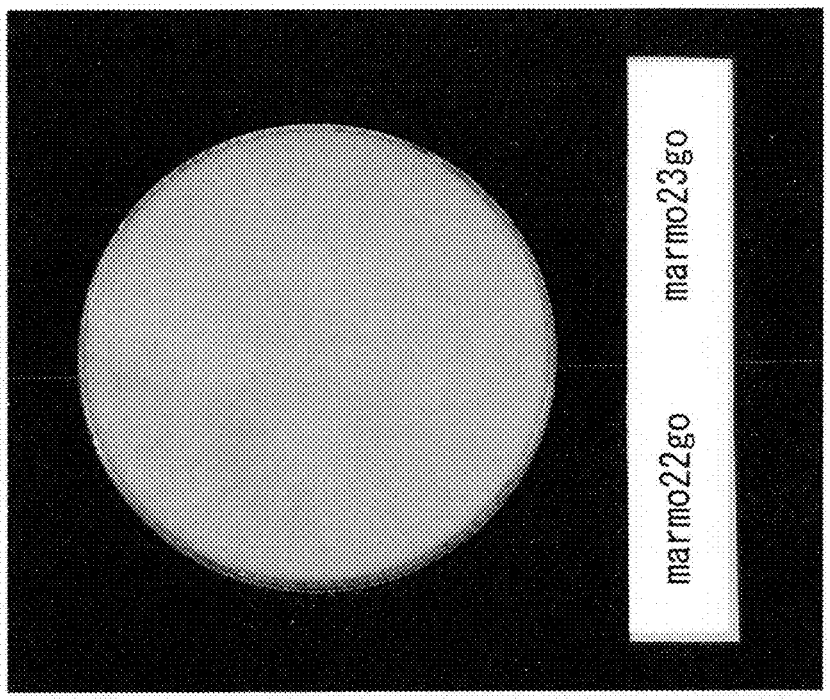
Figure 4B:
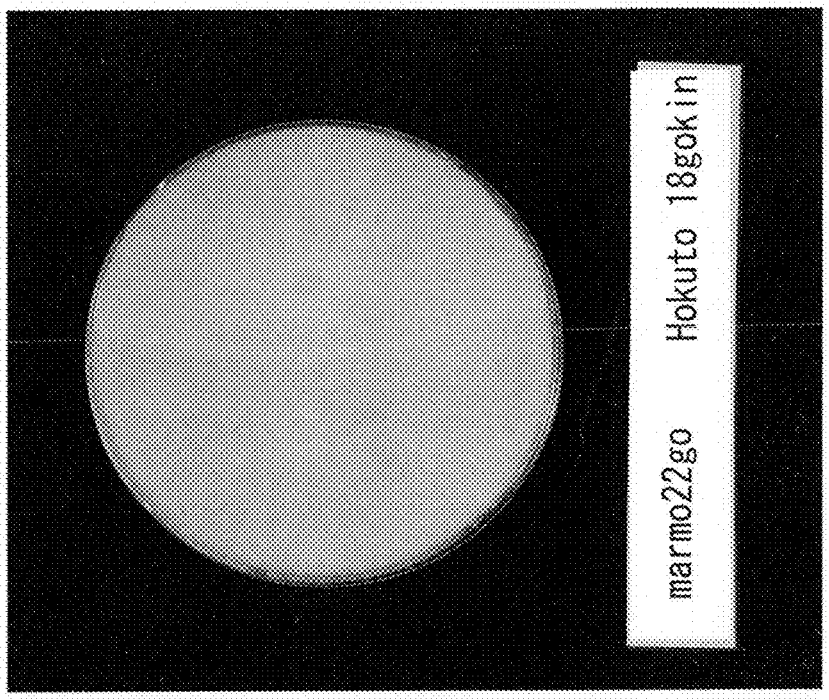
FIGS. 4A and 4B respectively show front and back images of a dual-culture of 'Marmo22go' and 'Hokuto 18gokin'.
Figure 4A:
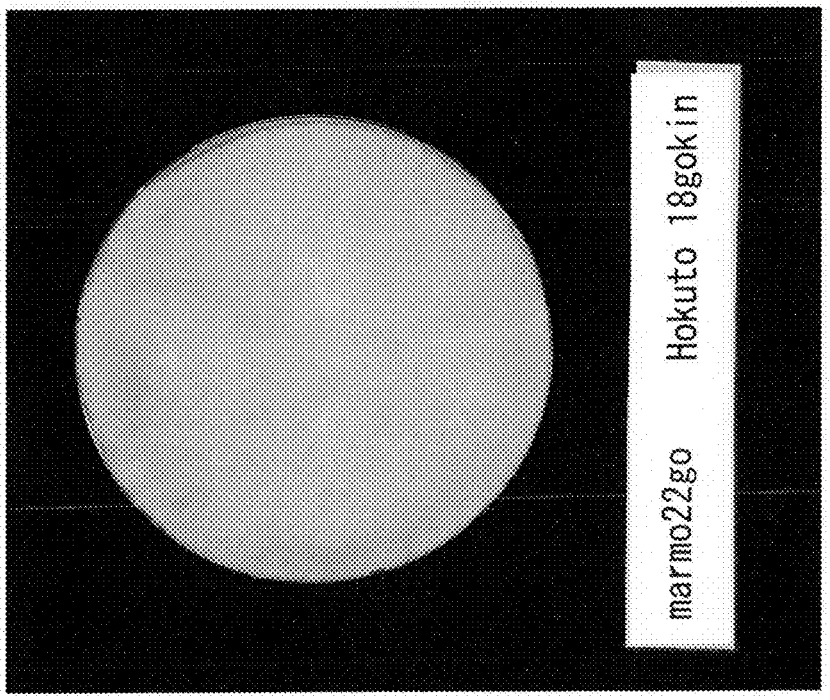
Figure 5A:
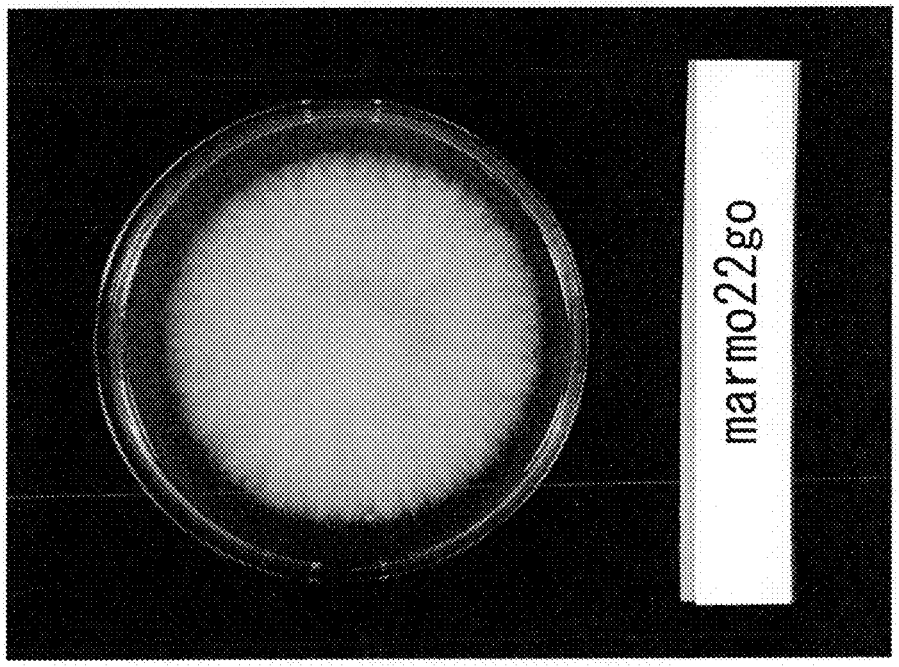
FIGS. 5A and 5B respectively show front and back images of fungal flora of 'Marmo22go'.
Figure 5B:
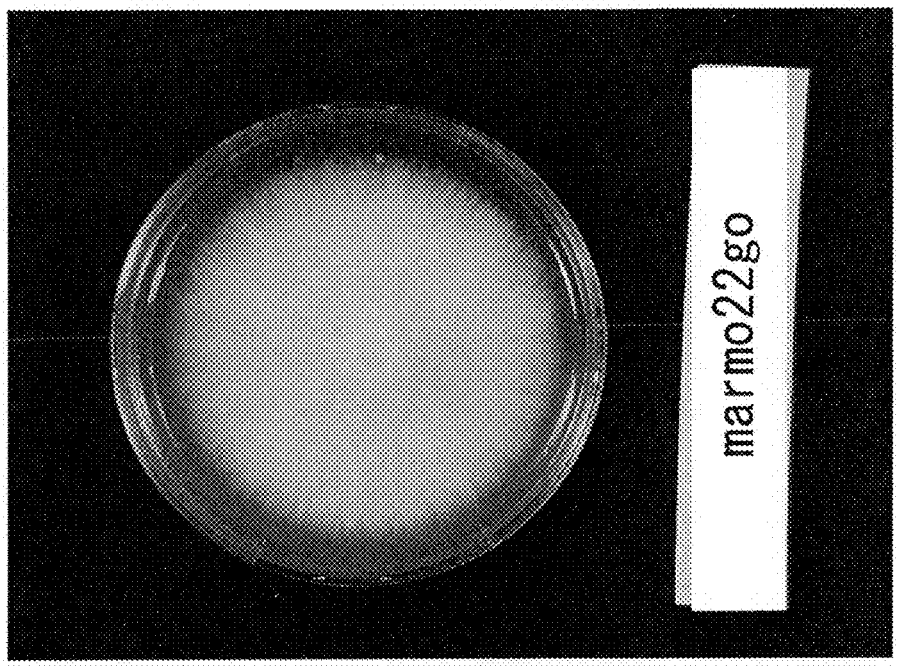
Figure 6A:
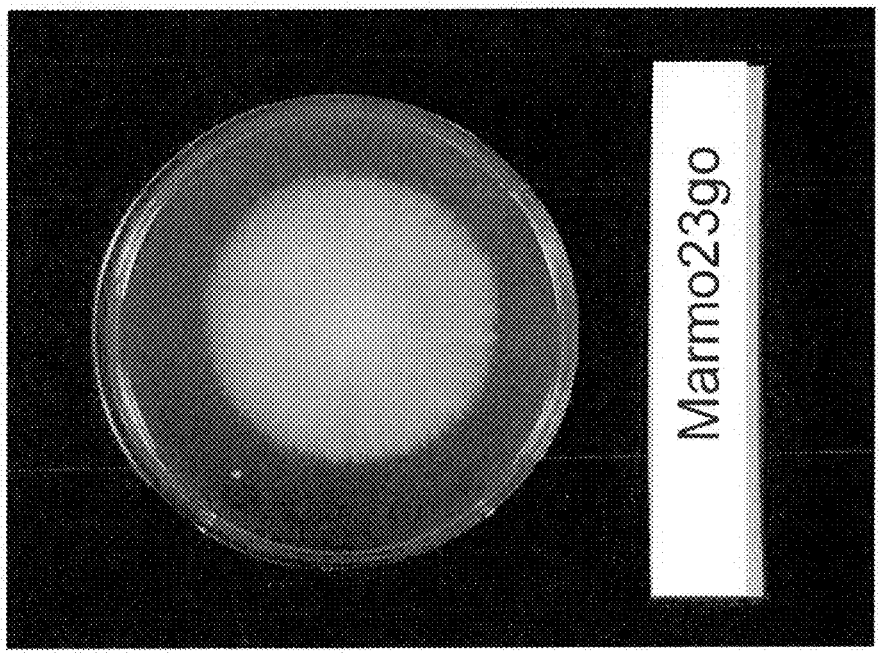
FIGS. 6A and 6B respectively show front and back images of fungal flora of 'Marmo23go'.
Figure 6B:
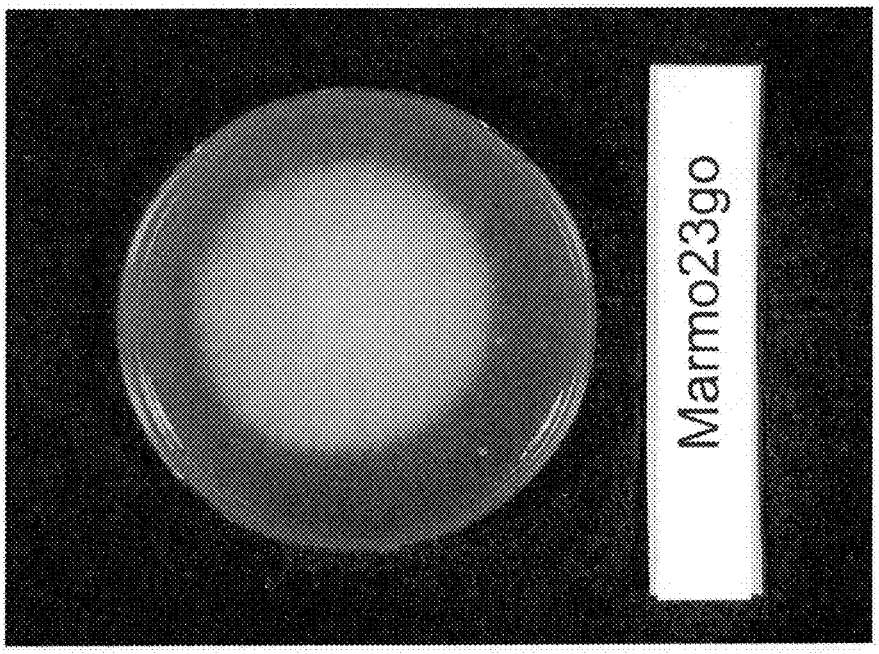
FIG. 6B Prior Art
Figure 7A:
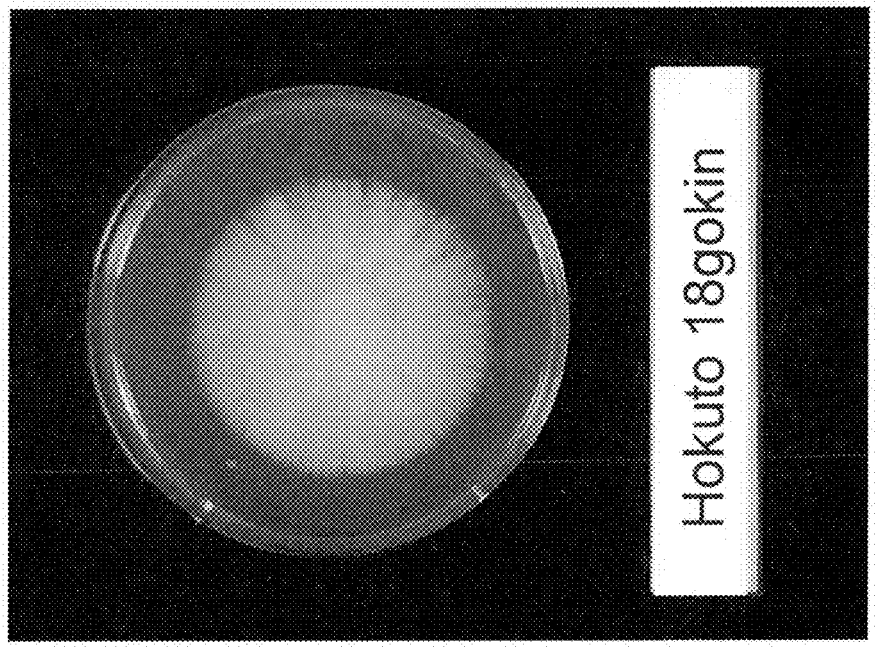
FIGS. 7A and 7B respectively show front and back images of fungal flora of 'Hokuto 18gokin'.
Figure 7B:
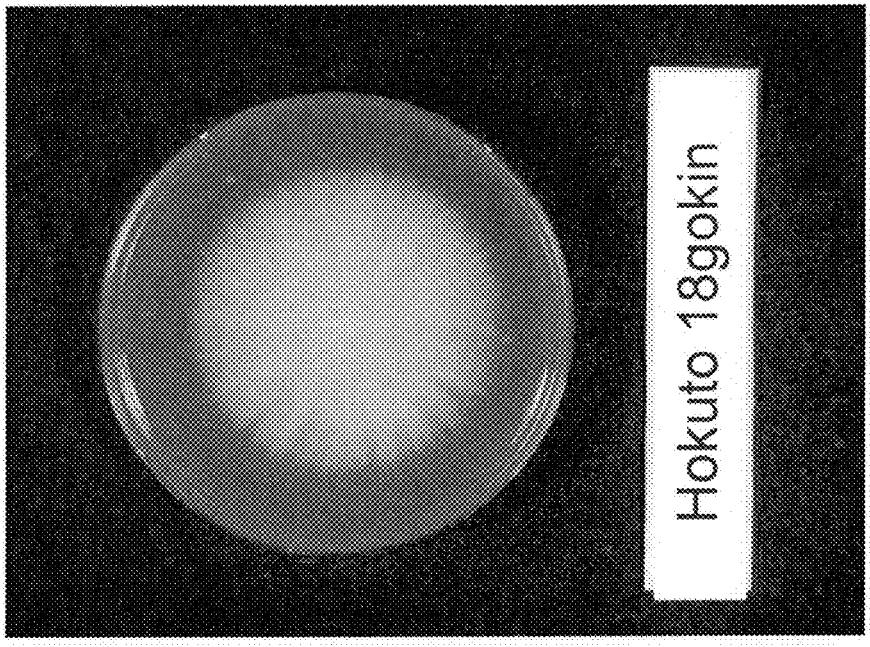
FIG. 7B Prior Art
Figure 8:
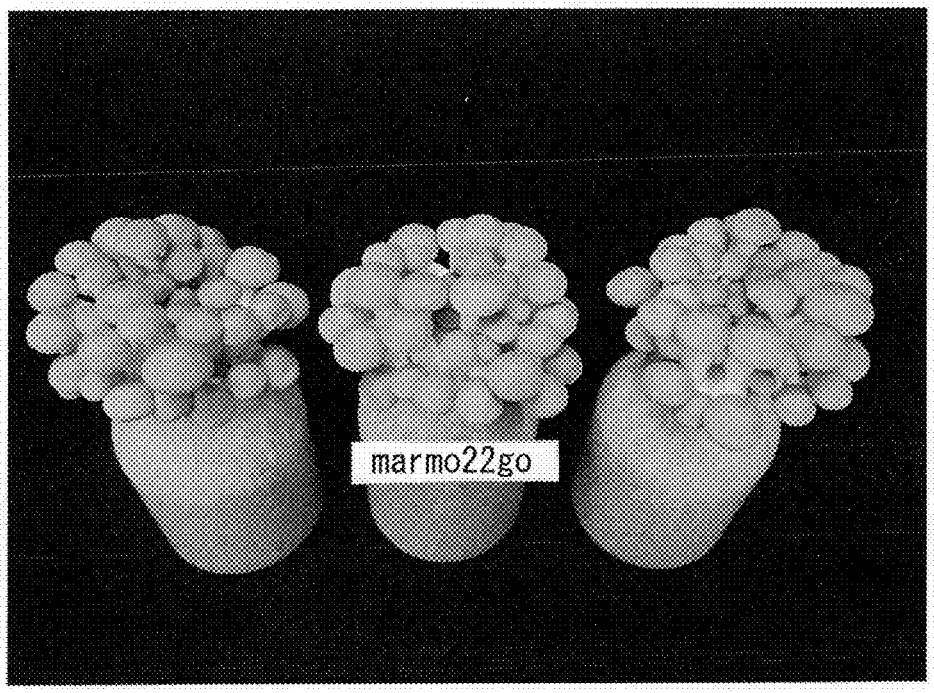
FIG. 8 shows an image of a fruit body of 'Marmo22go'.
Figure 9:
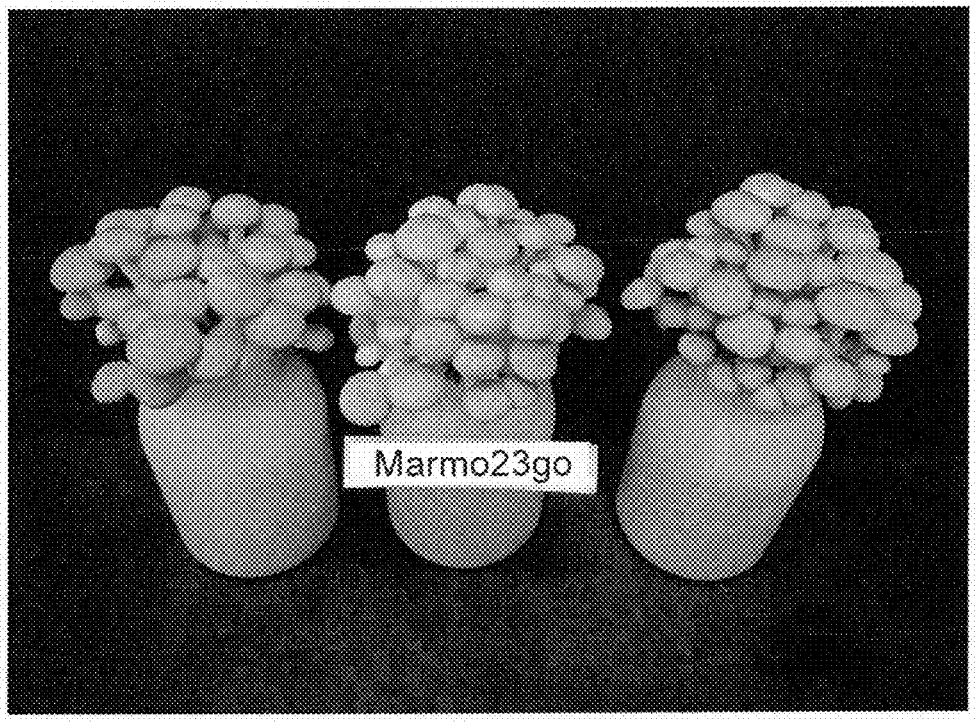
FIG. 9 Prior Art
FIG. 9 shows an image of a fruit body of 'Marmo23go'.
Figure 10:
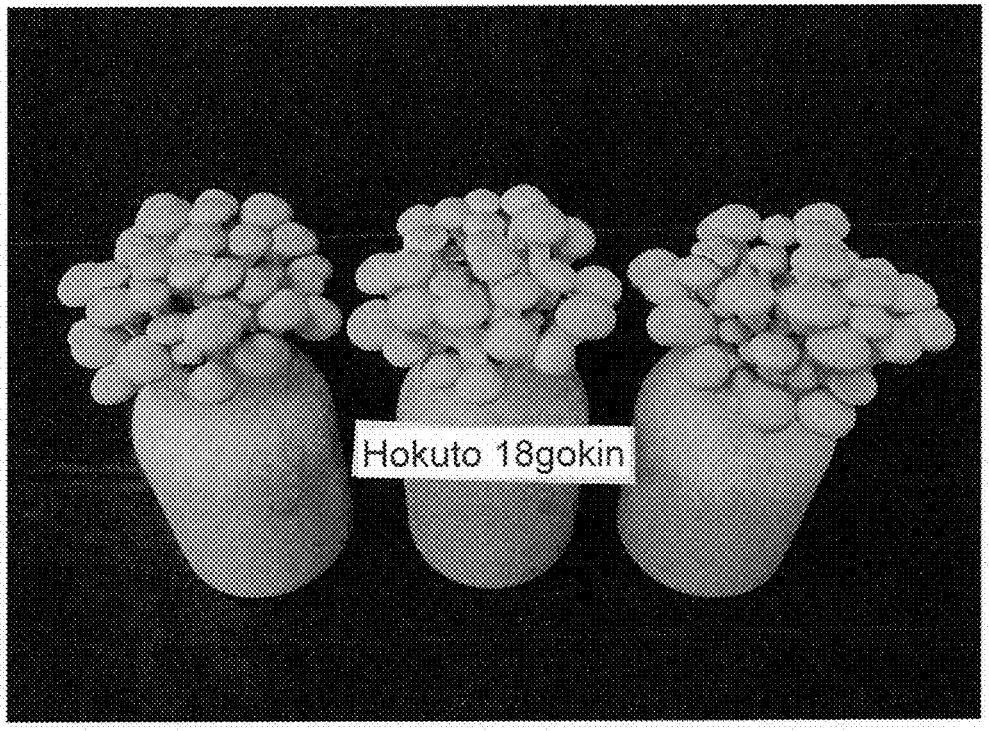
FIG. 10 Prior Art
FIG. 10 shows an image of a fruit body of 'Hokuto 18gokin'.
Figure 11:
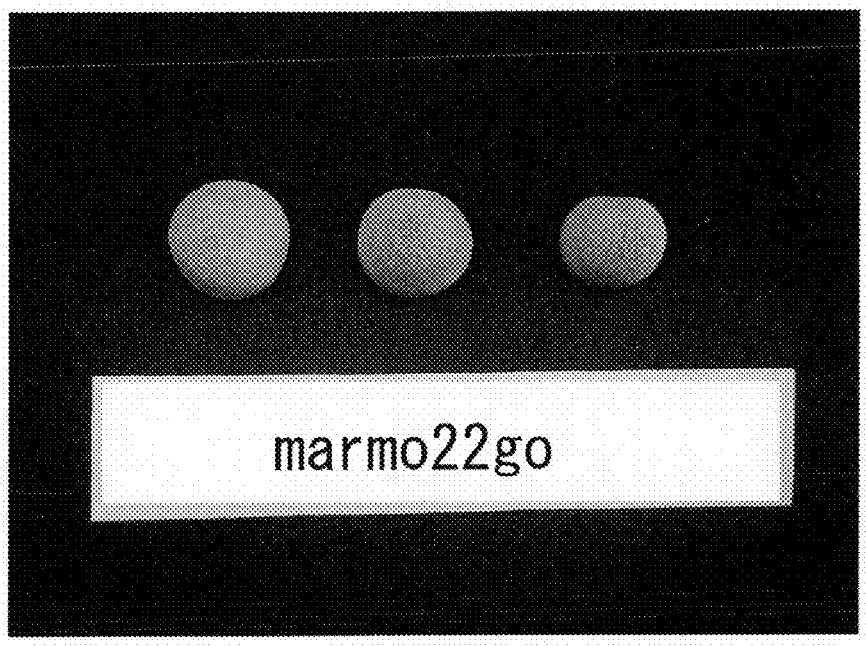
FIG. 11 shows an image of size of mottle of 'Marmo22go'.
Figure 12:
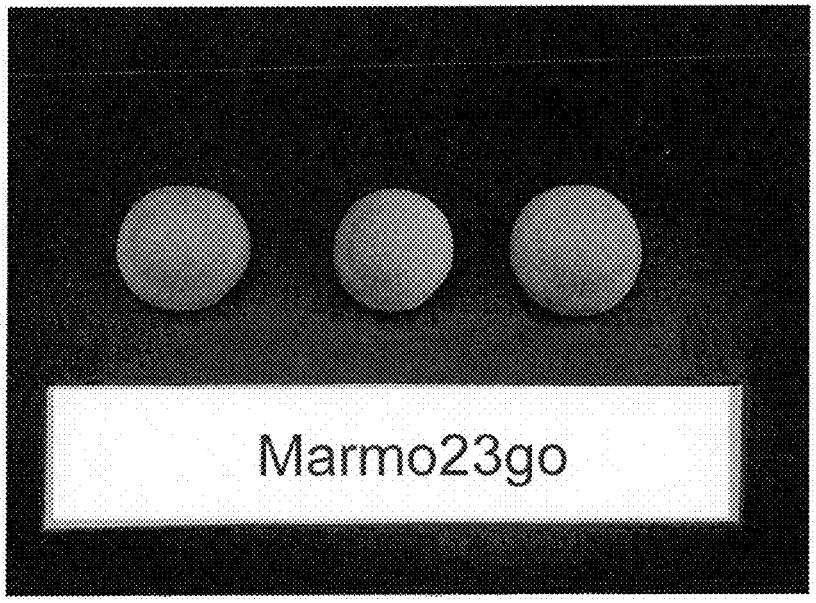
FIG. 12 Prior Art
FIG. 12 shows an image of size of mottle of 'Marmo23go'.
Figure 13:
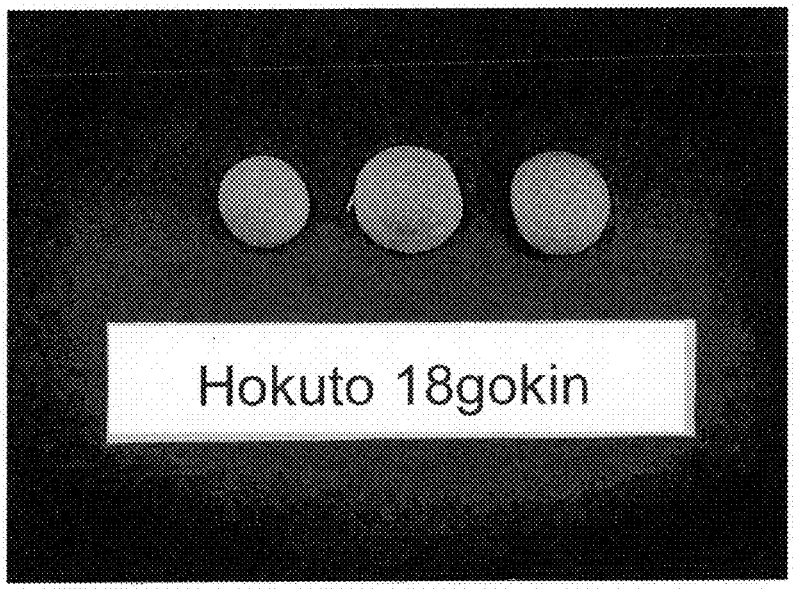
FIG. 13 Prior Art
FIG. 13 shows an image of size of mottle of 'Hokuto 18gokin'.
Figure 14:
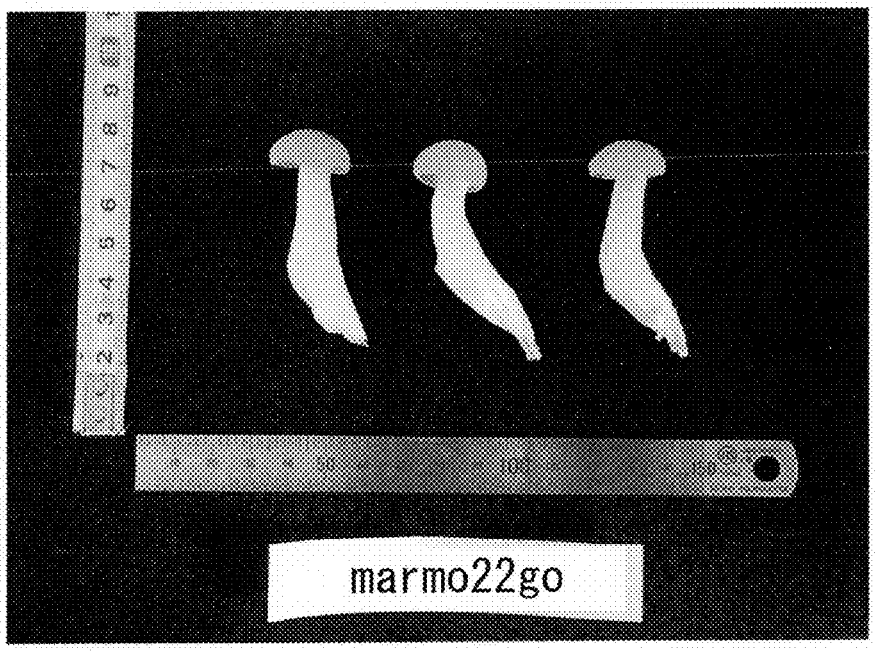
FIG. 14 shows an image of shape, length and size of stipe of 'Marmo22go'.
Figure 15:
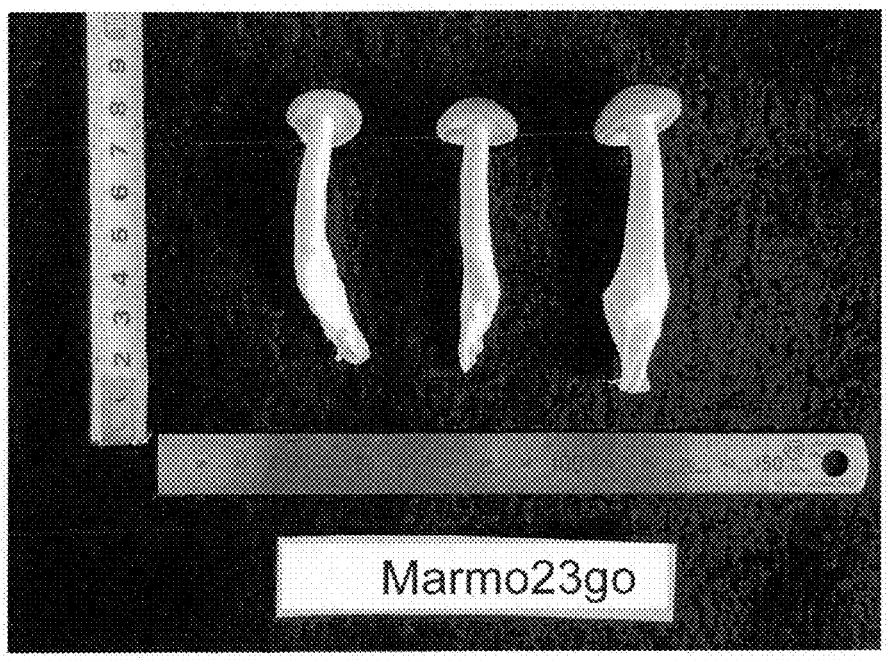
FIG. 15 Prior Art
FIG. 15 shows an image of shape, length and size of stipe of 'Marmo23go'.
Figure 16:
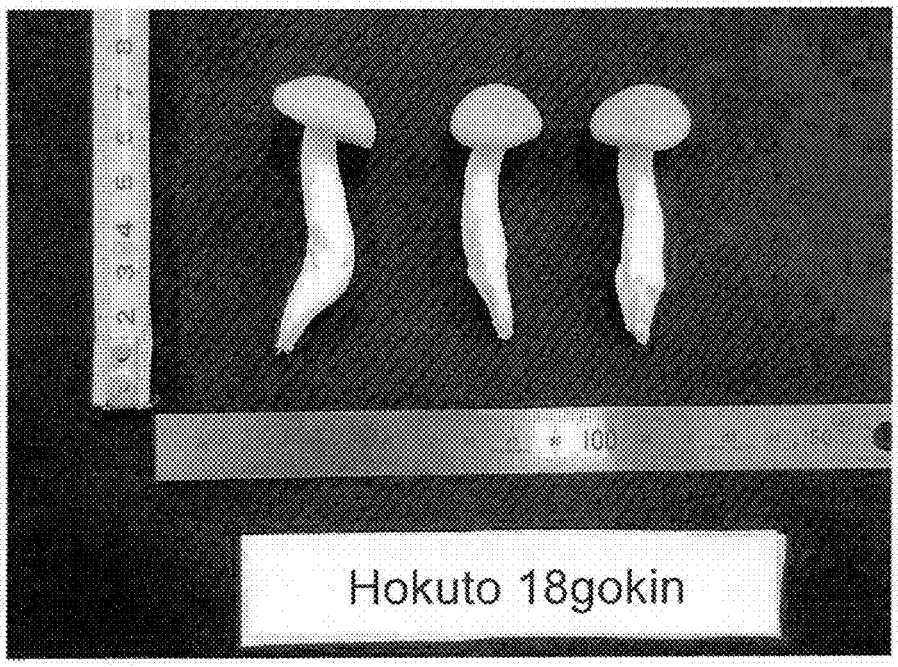
FIG. 16 Prior Art
FIG. 16 shows an image of shape, length and size of stipe of 'Hokuto 18gokin'.
Figure 17B:
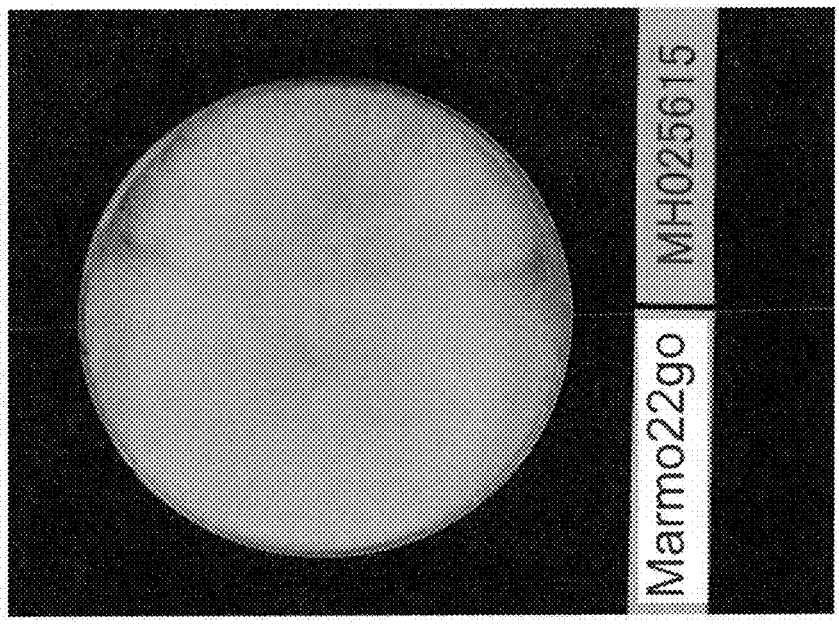
FIGS. 17A and 17B respectively show front and back images of a dual-culture of 'Marmo22go' and 'MH025615'.
Figure 17A:
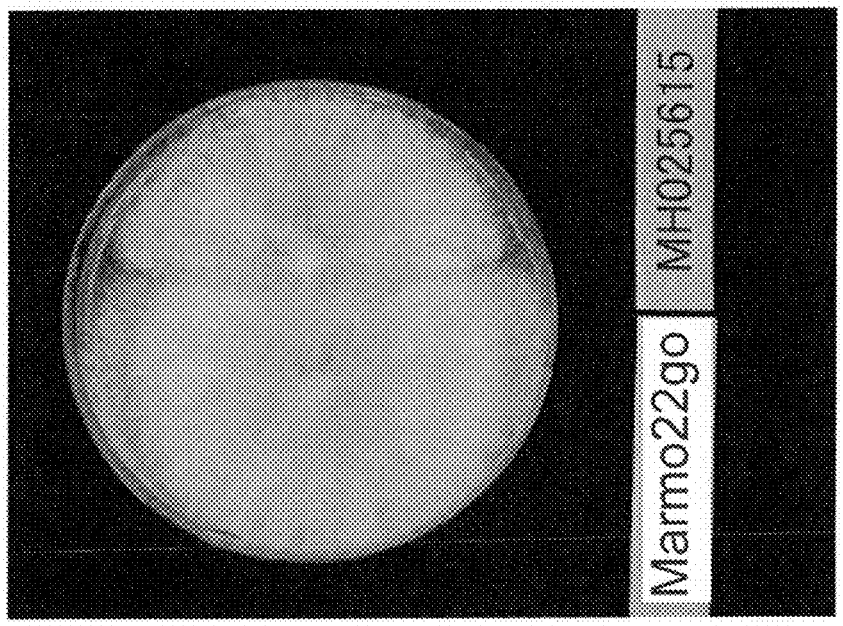
Figure 18B:
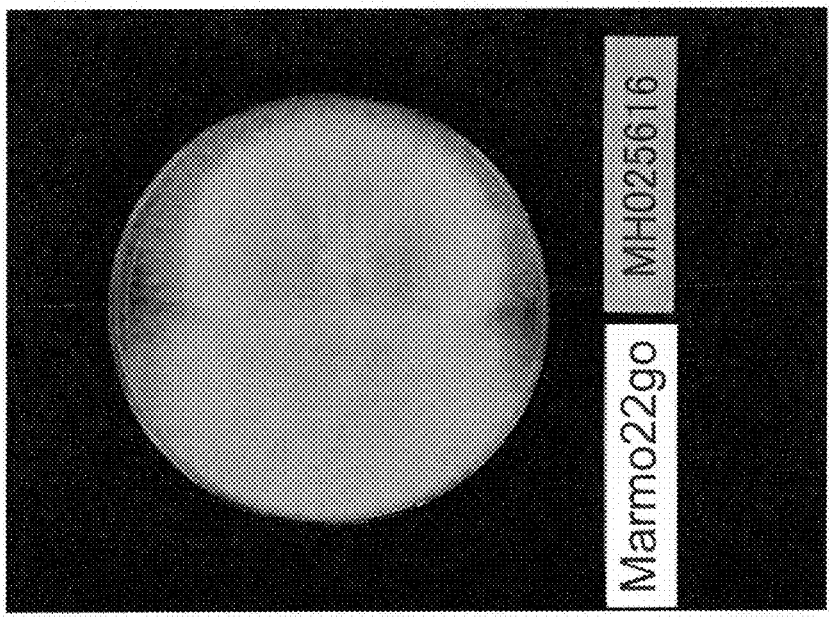
FIGS. 18A and 18B respectively show front and back images of a dual-culture of 'Marmo22go' and 'MH025616'.
Figure 18A:
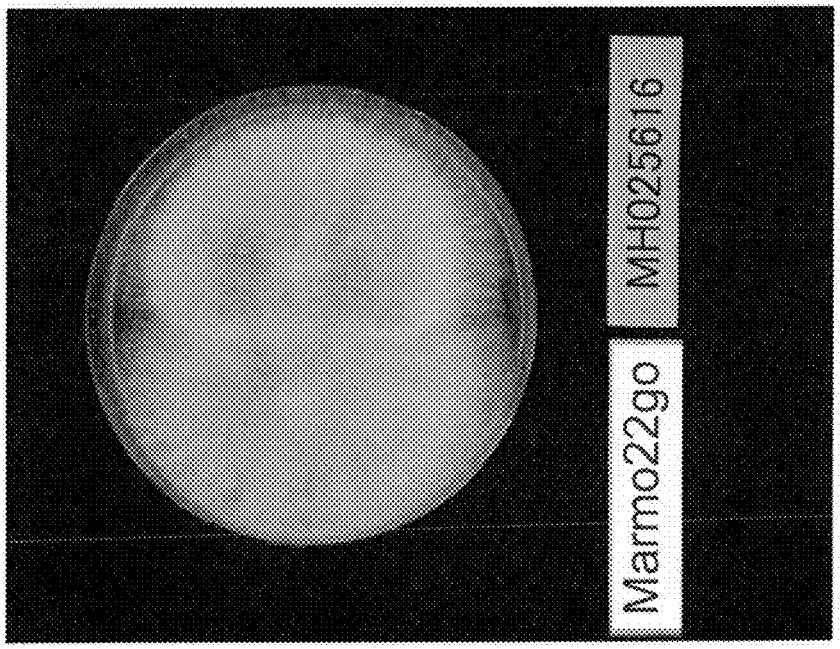

Results: Zone lines were formed between 'Marmo22go' and all other co-cultured varieties (Table 1, FIGS. 2 to 4). This clearly shows that the present mushroom is a new variety.

TABLE 1

| Results of dual culture | | |
|---|---|---|
| | Similar varieties | |
| | Marmo23go strain | Hokuto 18gokin |
| Marmo22go | + | + |

+ is present and − is absent.

*Zone line formation was not observed in the dual culture between 'Marmo22go' strains.

(2) Culture characteristics of 'Marmo22go'

Study method: After inoculating an agar piece of the 'Marmo22go' having a diameter of 5 mm in potato dextrose agar, preculture was performed at 25° C. for 4 days and hyphae were regenerated (about 10 mm in diameter), and then culture was performed for 7 days at intervals of 5° C. between 5° C. and 30° C. When the average daily hyphae growth rate was calculated based on a hyphae growth rate for seven days of the culture, it was found that the average hyphae growth rate of 'Marmo22go' was the fastest at 25° C. (See Table 2). Further, it was found that the hyphae growth rate of 'Marmo22go' was faster than that of 'Marmo23go' and 'Hokuto 18gokin' at 30° C. (See Table 2). 'Marmo22go' was asexually reproduced by inoculating on a potato dextrose agar at Mushroom Research Laboratory of the Hokuto Corporation in Nagano-shi, Nagano, Japan.

(3) Morphological characteristics of the 'Marmo22go' mushroom in a cultivation example Cultivation method:

*Container.*—An 850 polypropylene bottle (Capacity: 850 ml, diameter 58 mm) was used.

*Culture medium.*—Conifer sawdust, corn cob, rice bran and wheat bran were mixed at the dry weight ratio of 7:3:8:2, and the water content was adjusted to 65%. The culture medium was filled up to the brim of the bottle at the rate of 540±20 g per bottle, and was sterilized at high pressure.

*Starter culture.*—About 20 mL of sawdust starter cultures per bottle was inoculated.

*Culture.*—Culture was performed at 22° C. for 50 to 90 days at 70% moisture.

*Growth.*—After completing the culture, the inoculum is removed, and shifted to a growing room. Development was conducted under a temperature of 15±1° C., at humidity of 95% or more, without exposure to light particularly in the first 14 days, then after the 14th day, 500-1,000 Lx is taken and development is conducted at about 2,000 ppm $CO_2$ density. The mushroom is harvested when the cap in the center of the stump has sufficiently opened.

Cultivation results: Table 2 shows the characteristics of the 'Marmo22go' and specific difference in characteristics as compared with the similar varieties when culture was performed under the abovementioned conditions. Also, the whole images of the respective fruit bodies, the images of the respective mottles, and the images of the respective stipes have also been attached. (Refer to FIGS. 8 to 16).

TABLE 2

Fungus characteristics Table of *Hypsizygus marmoreus* (Peck) Bigelow of Recording and Registration

| | Present variety Marmo22go | Similar variety Marmo23go | Similar variety Hokuto 18gokin |
|---|---|---|---|
| Physiological property | | | |
| Dual culture | | | |
| Zone line formation | observed | observed | observed |
| Dislike-touch reaction | — | — | — |
| Density of hyphae | dense | dense | medium |
| Mycelial growth | dense | dense | medium |
| Color of surface of colony | white | white | white |
| Color of back of colony | pale yellow | pale yellow | pale yellow |
| Accommodativeness for temperature | | | |
| Optimal temperature for hyphal growth (° C.) | 24° C. | 24° C. | 24° C. |
| Hyphal growth rate | | | |
| 5° C./mm | 0.72 mm | 0.58 mm | 0.78 mm |
| 10° C./mm | 1.37 mm | 1.38 mm | 1.42 mm |
| 15° C./mm | 2.28 mm | 1.99 mm | 2.33 mm |
| 20° C./mm | 3.49 mm | 3.00 mm | 3.44 mm |
| 25° C./mm | 3.96 mm | 3.20 mm | 3.65 mm |
| 30° C./mm | 3.02 mm | 2.34 mm | 1.61 mm |
| Morphological property | | | |
| Cap | | | |
| Cross sectional shape | rounding mound | rounding mound | rounding mound |
| Mottle of the surface | medium | medium | medium |
| Size of mottle | small | small | medium |
| Distribution of mottle | whole | whole | whole |
| Clarity of mottle | very clear | very clear | very clear |
| Size (diameter) | 19.8 mm | 19.7 mm | 18.8 mm |
| Color of central area | grey-brown 199C | grey-brown 199A | grey-brown 199B |
| Color of peripheral area | grey-brown 199D | grey-brown 199B | grey-brown 199C |
| Thickness (mm) | 8.9 mm | 8.7 mm | 8.2 mm |
| Fleshy | medium | medium | medium |

TABLE 2-continued

Fungus characteristics Table of *Hypsizygus marmoreus* (Peck) Bigelow of Recording and Registration

| | Present variety Marmo22go | Similar variety Marmo23go | Similar variety Hokuto 18gokin |
|---|---|---|---|
| Gill | | | |
| Color | yellow-white 158C | yellow-white 158C | yellow-white 158C |
| Alignment | crinkle | crinkle | crinkle |
| Width | medium | medium | medium |
| Density | medium | medium | medium |
| Stipe | | | |
| Shape | medium thick | long and thin | medium thick |
| Length | 49.3 mm | 55.7 mm | 46.2 mm |
| Size (diameter) | 12.6 mm | 10.2 mm | 9.5 mm |
| Color | white 155B | white 155B | white 155B |
| Hair | absent | absent | absent |
| Fleshy | medium | medium | medium |
| Ratio of maximum diameter of stem to diameter just below cap | 1.61 mm | 1.68 mm | 1.55 mm |
| Cultural property | | | |
| Development of fruit body | | | |
| Development | strain | strain | strain |
| Optimal culture period | 70 days | 90 days | 90 days |
| Length of time from fruit body-formation promotion to fruit body harvesting at optimal temperature | 21.4 days | 21.1 days | 21.8 days |
| Optimal temperature for primordial development | 15° C. | 15° C. | 15° C. |
| Optimal temperature for fruit body growth | 15° C. | 15° C. | 15° C. |
| Yield | | | |
| Yield of fruit body | 133.8 g | 123.1 g | 117.6 g |
| The number of productive stem | 32.8 | 37.6 | 40.8 |

*The employed color chart is R.H.S. Colour Chart, 2007, Fifth edition, prescribed by Royal Horticultural Society, England.

What is claimed is:

1. A new, distinct variety of Bunashimeji mushroom as substantially illustrated and described in the specification.

* * * * *